United States Patent [19]
Wiersma et al.

[11] Patent Number: 6,046,023
[45] Date of Patent: Apr. 4, 2000

[54] MICROBIAL 11α-HYDROXYLATION OF STEROIDS

[75] Inventors: Marten Wiersma, Wilhelminalaan; Peter van der Meijden, Lisztgaarde, both of Netherlands

[73] Assignee: Akzo Nobel, N.V., Arnhem, Netherlands

[21] Appl. No.: 09/077,982

[22] PCT Filed: Dec. 10, 1996

[86] PCT No.: PCT/EP96/05729

§ 371 Date: Sep. 30, 1998

§ 102(e) Date: Sep. 30, 1998

[87] PCT Pub. No.: WO97/21830

PCT Pub. Date: Jun. 19, 1997

[30] Foreign Application Priority Data

Dec. 12, 1995 [EP] European Pat. Off. ............... 95203451

[51] Int. Cl.⁷ ................. C12P 33/10; C07J 1/00; C07J 21/00

[52] U.S. Cl. ................. 435/60; 540/43; 552/621

[58] Field of Search ............... 540/43; 552/621; 435/60

[56] References Cited

U.S. PATENT DOCUMENTS 2,602,769  7/1952  Murray et al. ............................. 195/51
3,294,646  12/1966  Smith et al. ............................. 195/51

OTHER PUBLICATIONS

Tan et al., *J. Steroid Biochem*, 1(3):221–227, 1970.

*Primary Examiner*—Jose C. Dees
*Assistant Examiner*—Barbara Badio
*Attorney, Agent, or Firm*—Mary E. Gormley

[57] ABSTRACT

The invention relates to a microbial method of in vitro transformation of a steroid into its corresponding 11α-hydroxy analogue using oxygen and a microorganism selected from the *Aspergillus ochraceus, Aspergillus niger, Rhizopus stolonifer, Rhizopus nigricans, Rhizopus arrhizus*, and strains of Pestelotia, using as substrate a steroid having a purity of less than 97% and more than 90% at a concentration greater than 10 g/l.

4 Claims, No Drawings

MICROBIAL 11α-HYDROXYLATION OF STEROIDS

This application is a 371 of PCT/EP96/05729 filed Dec. 10, 1996.

FIELD OF THE INVENTION

The present invention relates to a microbial method of 11α-hydroxylation of steroids.

BACKGROUND OF THE INVENTION

Microbial 11α-hydroxylation of steroids is a well known process, in vivo as well as in vitro. For instance 11α-hydroxylation of progesterone by cell-free preparations of *Aspergillus ochraceus* has been reported by Shibahara et al., Biochim. Biophys. Acta, 202 (1970), 172–179. It has also been known that microbial 11α-hydroxylation reactions of steroids are unpredictable, and invariably lead to incomplete transformations. Typically conversion degrees of 80–85% are obtained. For industrial applications it is however of importance to obtain high predictable conversion rates, which preferably lead to higher than 95% yields of 11α-hydroxylated steroids. Mathematical models in the optimization of such fermentation processes are discussed by Deshayes et al., Bull. Soc. Chim. Fr., (1980), II 24–34. For example, in the 11α-hydroxylation of canrenone, Deshayes disclosed that under optimum conditions better than 95% yields could be attained when *Aspergillus ochraceus* was used in a medium containing i.a. 10 g/l of glucose in a matrix of malt-extract and trypticase. Under these conditions up to 1.5 g/l of canrenone could be transformed, which was considered to be an improvement in the art, for instance as disclosed by Blunt et al., J. Chem. Soc., 6 (1971), 1136, who were not able to obtain more than 90% yield of 11α-hydroxylated canrenone using at the most 0.5 g/l of substrate.

SUMMARY OF THE INVENTION

Since it can be reasoned that contaminations will have a detrimental influence on the microbial process, it can be expected that further optimization could be obtained by increasing the purity of the starting materials. Surprisingly however, it has now been found that a further improvement is obtained by using less than pure substrate, in particular by using a substrate having a purity of less than 97%. The invention therefore relates to a microbial method of in vitro transformation of a steroid into its corresponding 11α-hydroxy analogue using oxygen and a micro-organism selected from *Aspergillus ochraceus, Aspergillus niger, Rhizopus stolonifer, Rhizopus nigricans, Rhizopus arrhizus,* and strains of Pestelotia, characterized in that a steroid having a purity of less than 97% is used.

Preferably the microorganism is *Aspergillus ochraceus*. The purity of the steroid is preferably more than 90%. More preferably the purity of the steroid is between 90 and 95%. The present method using impure substrates affords microbial transformations at substrate concentrations, which are substantially greater than the maximum concentrations as disclosed by blunt or Deshayes.

DETAILED OF DESCRIPTION OF THE INVENTION

The present microbial method can be used with steroids having an unsubstituted 11-position. Preferred examples are estr-4-ene-3,17-dione and canrenone.

The surprising effect of impurities on the conversion degree is illustrated in the following tables.

TABLE I

Conversion of estr-4-ene-3,17-dione by *A. ochraceus*

| purity (%) | substrate concentration (g/l) | conversion degree (%) |
|---|---|---|
| 99 | 15 | 78 |
| 99 | 10 | 83 |
| 98 | 25 | 85 |
| 94* | 15 | 91 |
| 94* | 15 | 91 |
| 94* | 15 | 94 |
| 93 | 25 | 97 |
| 92 | 10 | 98 |

*various natural impurities added to pure substrate

TABLE II

Conversion of canrenone by *A. ochraceuis*

| purity (%) | substrate concentration (g/l) | conversion degree (%) |
|---|---|---|
| 100 | 5 | 74 |
| 100 | 10 | 78 |
| 100 | 20 | 73 |
| 100 | 35 | 72 |
| 96 | 10 | 98 |
| 94 | 15 | 96 |
| 96 | 22 | 96 |
| 95 | 22 | 95 |

The invention is further illustrated by the following examples.

EXAMPLES

Example 1

A shake flask containing a mineral growth medium with glucose was inoculated with spores of *A. ochraceus* and placed on a reciprocal shaker at 28° C. for 15 h. A stirred fermentor containing 5 l of medium was subsequently inoculated with 250 ml of germinated spore suspension. The used medium contained a glucose/yeast extract medium (glucose 40 g/l, yeast extract 10 g/l, pH 5.0). The culture conditions were as follows: stirrer speed 750 rpm, airflow 0.2 l/l/m, temp 28° C. Foaming was measured with an antifoam electrode and controlled by automatic addition of a silicon based antifoam agent. When the culture had a biomass concentration of at least 2 g/l a small portion of estr-4-ene-3,17-dione (1 g/l) was added to induce the synthesis of the hydroxylation enzymes. Three hours later higher concentrations of steroid were added to reach the desired concentrations as given in Table I. The steroid transformation was stopped when repeatedly no increase in conversion was observed.

Example 2

In a shake flask the same culture as described in Example 1 was prepared. When the culture had a biomass concentration of at least 4 g/l the canrenone was added at once to reach the desired concentrations as given in Table II. The steroid transformation was stopped when repeatedly no increase in conversion was observed.

We claim:

1. In a microbial method of in vitro transformation of a steroid selected from estr-4-ene-3,17-dione and canrenone into its corresponding 11α-hydroxy analogue using oxygen and a microorganism selected from the *Aspergillus ochraceus, Aspergillus niger,, Rhizopus stolonifer, Rhizopus nigricans, Rhizopus arrhizus*, and strains of Pestelotia, the improvement comprising using as substrate a steroid having a purity of less than 97% and more than 90% at a concentration greater than 10 g/l.

2. The method according to claim 1, wherein the microorganism is *Aspergillus ochraceus*.

3. The method according to claim 1, wherein the purity of the steroid is between 90 and 95%.

4. The method according to claim 2, wherein the purity of the steroid is between 90 and 95%.

* * * * *